United States Patent
Osaka

(10) Patent No.: US 7,862,724 B2
(45) Date of Patent: Jan. 4, 2011

(54) PREPARATIVE LIQUID CHROMATOGRAPH SYSTEM AND PREPARATIVE SEPARATION/PURIFICATION METHOD USING THE SAME

(75) Inventor: Naoki Osaka, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 12/486,349

(22) Filed: Jun. 17, 2009

(65) Prior Publication Data

US 2009/0314716 A1 Dec. 24, 2009

(30) Foreign Application Priority Data

Jun. 24, 2008 (JP) ............... 2008-163995

(51) Int. Cl.
*B01D 15/08* (2006.01)
(52) U.S. Cl. .................... 210/656; 210/198.2
(58) Field of Classification Search ......... 210/635, 210/656, 96.1, 101, 143, 198.2
See application file for complete search history.

(56) References Cited

U.S. PATENT DOCUMENTS

| | | | |
|---|---|---|---|
| 4,468,331 A * | 8/1984 | Antle et al. | 210/659 |
| 4,775,476 A * | 10/1988 | Melcher et al. | 210/635 |
| 4,861,488 A * | 8/1989 | Kenney et al. | 210/656 |
| 5,436,166 A * | 7/1995 | Ito et al. | 436/161 |
| 6,428,704 B1 * | 8/2002 | Setoguchi et al. | 210/635 |
| 2006/0213838 A1 * | 9/2006 | Iwata et al. | 210/656 |

FOREIGN PATENT DOCUMENTS

| | | |
|---|---|---|
| JP | 02-122260 A | 5/1990 |
| JP | 2003-149217 A | 5/2003 |
| JP | 3864876 B2 | 1/2007 |

OTHER PUBLICATIONS

PTO 10-4654 of Japan Patent No. 02122260.*
PTO 10-4652 of Japan Patent No. 3864876.*
PTO 10-4653 of Japan Patent No. 2003149217.*

* cited by examiner

*Primary Examiner*—Ernest G Therkorn
(74) *Attorney, Agent, or Firm*—Sughrue Mion, PLLC

(57) ABSTRACT

A technique for extracting an objective component from a sample solution and obtaining the component in the form of equally separated powder aliquots is provided. A peak detector 12 detects the start point of the peak of the objective component on a chromatogram created from detection signals produced by a detector 5. Then, a controller 14 immediately changes a valve 6 so that the eluate will flow to a trap column 7a. A peak area processor 13 calculates the peak area of the objective component in real time. When the calculated area has exceeded a threshold, the controller 14 changes the valve 6 so that the eluate will flow to the next trap column 7b. Thus, the trap columns 7a to 7d are sequentially selected to divide the peak into one or more portions with the same area so that the objective component in the eluate will be sequentially captured by the trap columns 7a to 7d. Subsequently, the objective component is eluted from each trap column, and then the solvent is vaporized, to obtain powder of the objective component.

8 Claims, 3 Drawing Sheets

PREPARATIVE LIQUID CHROMATOGRAPH SYSTEM AND PREPARATIVE SEPARATION/PURIFICATION METHOD USING THE SAME

The present invention relates to a preparative liquid chromatograph (LC) system including a plurality of trap columns for capturing a sample component separated by a column of a liquid chromatograph, and a preparative separation/purification method using this system.

BACKGROUND OF THE INVENTION

For example, preparative separation/purification systems including a liquid chromatograph are used in the pharmaceutical industry to collect samples of a variety of chemically synthesized compounds in order to store those samples into a library or analyze them in more detail. Conventional examples of the preparative separation/purification systems are disclosed in Japanese Unexamined Patent Application Publication Nos. H02-122260, 2003-149217 and other documents.

In these conventional apparatuses, objective components (compounds) in a sample solution are temporally separated by a liquid chromatograph. The separated objective components are then respectively introduced into different trap columns and temporarily captured therein. Subsequently, a solvent is supplied into each trap column to quickly elute the component from the trap column and collect it in a container. Thus, a plurality of solutions each containing one objective component at a high concentration are respectively collected in a plurality of containers. These separately collected solutions are then subjected to a vaporizing and drying process to remove the solvent and collect the objective components in solid forms. The vaporizing and drying process normally includes heating the collected solutions or centrifuging them under vacuum.

In this preparative separation/purification process, it has been desired in some cases that a component contained in the sample solution by a relatively large amount should be accurately separated into equal aliquots and collected in the form of small solids rather than a single mass. This requirement cannot be met, for example, by separating the eluate into equal volumes in the preparative separation process of the eluate containing the objective component; what is necessary is to control the volume of each aliquot of the eluate so that every aliquot contains the same amount of the objective component.

Japanese Patent No. 3864876 discloses a preparative LC system designed for separating an eluate into a plurality of containers in such a manner that every separate sample contains the same amount of the objective component. This preparative LC system monitors the height of peaks appearing on a chromatogram and controls the sampling operation so that the amount of the eluate to be collected in the container will be decreased for higher peaks. Controlling the volume of the aliquot of the eluate according to the peak height will work if the peak shape is comparatively normal and clear, but will not yield good results if the peak shape is abnormal and distorted. For example, if the curve on the anterior side of the peak top is not monotonically increasing or the curve on the posterior side of the peak top is not monotonically decreasing, the amounts of the objective component in the separately sampled solutions are likely to be significantly dispersed.

The preparative separation apparatus described in Japanese Patent No. 3864876 uses test tubes or similar containers to collect the sample. In this case, if the sample has a low concentration of the objective component, it is necessary to collect a large amount of the eluate in the container, which possibly causes the eluate to exceed the capacity of the container and overflow.

The present invention has been developed in view of the previously described problems. Its first objective is to provide a preparative LC system capable of more accurately separating an objective component into equal aliquots, regardless of the peak shape, without causing an overflow or other problems of an eluate even if the concentration of the objective component is low. The second objective of the present invention is to provide a preparative separation/purification method capable accurately separating an objective component in a sample solution into equal aliquots and collecting them in solid forms.

SUMMARY OF THE INVENTION

To achieve these objectives, the present invention provides a preparative liquid chromatograph system having a liquid chromatograph including a separation column for separating a component from a sample and a detector for detecting the component contained in an eluate coming from the separation column, a plurality of trap columns for trapping the component contained in the eluate, and a channel selector for switching a channel so that the eluate is selectively supplied to one of the trap columns. The system further includes:

a) a chromatogram creator for creating a chromatogram during a chromatographic analysis of the sample, based on a detection signal produced by the detector;

b) a peak area calculator for performing a real-time calculation of the area value of a peak of an objective component appearing on the chromatogram, the calculation starting from a point in time where the channel is switched by the controller to be mentioned below; and c) a controller for controlling the channel selector so that the destination of the eluate coming from the separation column is changed from one trap column to another every time the area value calculated by the peak area calculator reaches a predetermined value.

In a preferable mode of the preparative liquid chromatograph system according to the present invention, the system further includes an input section for setting the quantity of the objective component to be captured in each trap column, and the controller determines, based on the quantity that has been set through the input section, a reference value for making a determination on the area value calculated by the peak area calculator.

The present invention also provides a preparative separation/purification method using the preparative liquid chromatograph system according to the present invention. The method includes:

a separation process in which an objective component is captured in each of the trap columns by the preparative liquid chromatograph system;

an elusion process in which a solvent is supplied to each of the trap columns to elute the objective component captured in the trap columns; and a collection process in which the solvent contained in the eluate coming from the trap columns is vaporized to collect the objective component in a solid form for each of the trap columns.

The preparative liquid chromatograph system according to the present invention controls the supply of an eluate to the trap columns according to the peak area of the objective component calculated by the peak area calculator, and not according to the peak height. The peak area correctly reflects the amount of the objective component contained in the eluate. Accordingly, the preparative liquid chromatograph system according to the present invention can accurately equalize the quantity of the objective component to be collected in each of the trap columns.

When an eluate is supplied to a trap column, the objective component contained in the eluate is captured, for example, by the packing material within the trap column. After the objective component is thus removed, the eluate passes through the trap column, to be eventually discharged. As compared to the conventional system using containers to collect the eluate, the present system is advantageous in that the overflow problem of the eluate cannot occur even if a large amount of eluate is supplied to a single trap column (the eluate is normally supplied at a constant rate and hence requires a long supply time). Accordingly, the preparative liquid chromatograph system according to the present invention can accurately capture an intended quantity of the objective component in every trap column, regardless of the concentration of the objective component in the sample.

The preparative separation/purification method according to the present invention provides a simple way of obtaining equal quantities of an objective component in solid forms, thus making it easy to prepare a medicine, reagent or similar product containing a specific component by an equal quantity.

DETAILED DESCRIPTION OF A PREFERRED EMBODIMENT

A preparative LC system, which is an embodiment of the present invention, and a preparative separation/purification method using this system, are hereinafter described with reference to the attached drawings.

Figure 4:
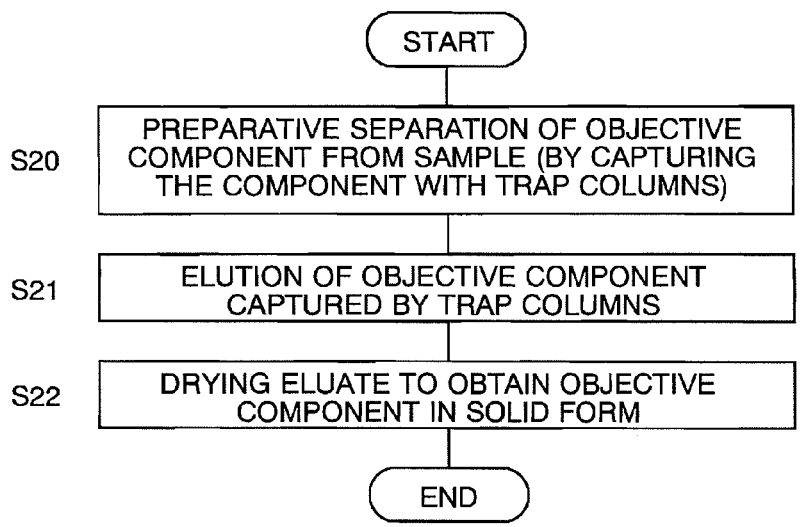
FIG. 4 is a flowchart showing the steps of separating and purifying an objective component by the preparative LC system of the present embodiment.

First, the process of preparative separation/purification of an objective component by the preparative LC system of the present embodiment is described along the flowchart of FIG. 4.

In the initial step, a sample containing impurities in addition to the objective component is separated into the components by the liquid chromatograph. The objective component is then separated into aliquots each having the same specified quantity, and these aliquots are individually captured by the trap columns (Step S20). This process of separating the objective component uses the preparative LC system to be described later. In the next step, the objective component captured in each trap column is eluted by supplying a solvent into the trap column (Step S21). In this step, the objective component captured in the trap column can be completely eluted in a short time, i.e. with a small amount of the solvent, by using a solvent having a high elusion capability.

Then, the collected eluate is heated to accelerate the vaporization of the solvent and collect dry powder of the objective component (Step S22). A higher concentration of the objective component in the eluate reduces the vaporization time of the solvent and hence enhances the process efficiency. Since the objective component has been separately collected in each of the trap columns by the specified quantity in Step S20, the objective component obtained in Step S22 will be in the form of aliquots each having the specified quantity.

Figure 1:
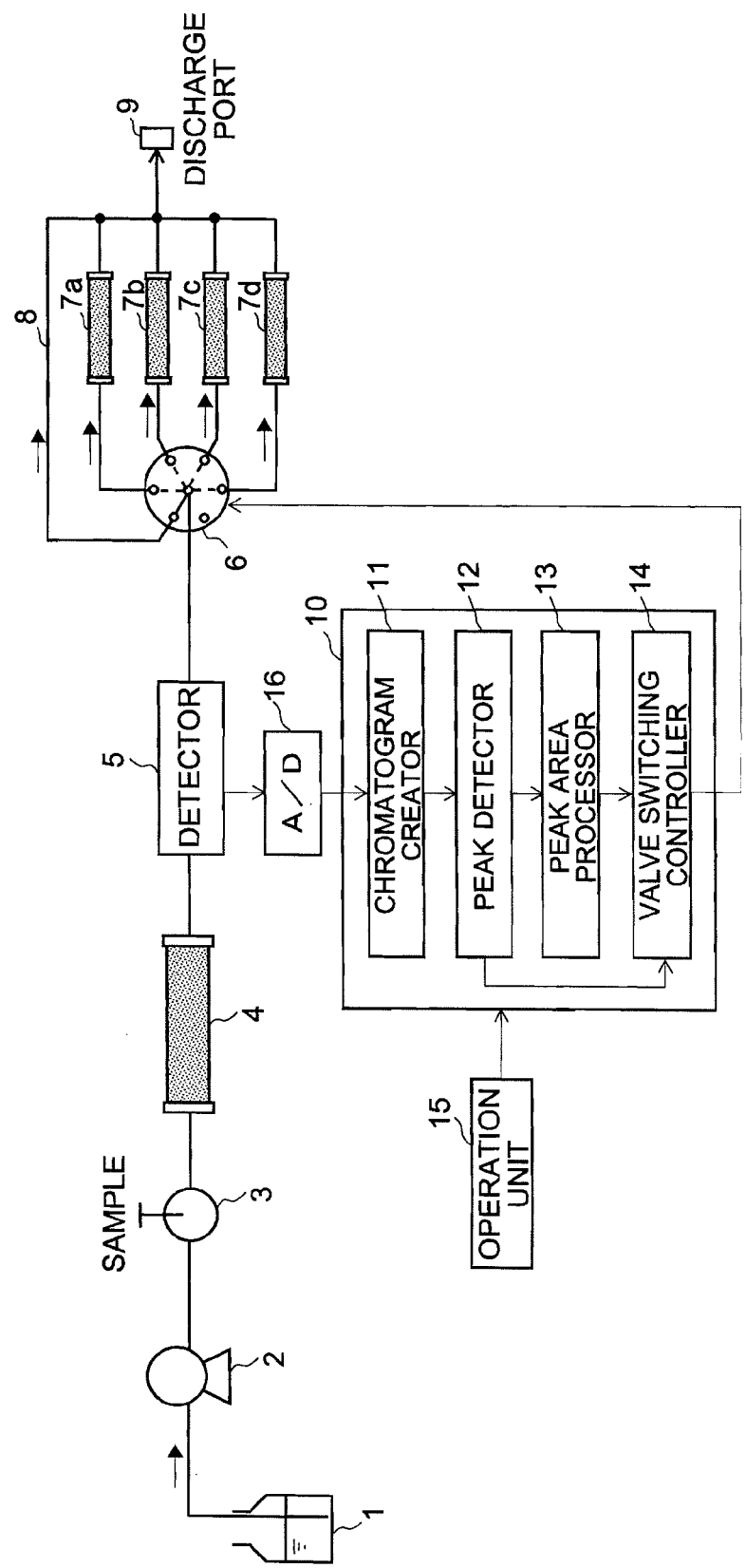
FIG. 1 is a schematic configuration diagram of a preparative LC system according to one embodiment of the present invention.

FIG. 1 is a schematic configuration diagram of the preparative LC system according to the present embodiment. In this preparative LC system, a mobile phase contained in a mobile phase container 1 is drawn by a liquid supply pump 2 and fed through an injector 3 into a separation column 4 at a constant flow rate. When a sample is injected into the mobile phase at the injector 3, the sample is carried by the mobile phase into the separation column 4. While the sample is passing through the column 4, the components in the sample are eluted in a temporally separated form. For example, if the sample contains impurity components as well as an objective component, the objective component will be separated from the other while passing through the column 4, and each component will be detected with a different retention time in the eluate.

The detector 5 is, for example, an ultraviolet-visible spectrophotometer and produces a detection signal corresponding to the component contained in the eluate coming from the separation column 4. After passing through the detector 5, the eluate is either entirely or partially supplied via a channel selection valve 6 to either one of a plurality of trap columns (four trap columns 7a to 7d in this embodiment) or a drain channel 8, and eventually reaches a discharge port 9. The trap columns 7a to 7d are each packed with a material for capturing the objective component. The number of trap columns is four in this embodiment but not limited to this number.

The analogue detection signals produced by the detector 5 are converted into digital values at predetermined intervals of sampling time ST by an A/D converter 16 and fed to a processing/controlling unit 10. The processing/controlling unit 10 performs data processing to be described later and controls the operation of switching the channel selection valve 6 according to the result of the data processing. This unit 10 includes various functional blocks, including a chromatogram creator 11, peak detector 12, peak area processor 13 and valve switching controller 14. In terms of hardware configuration, the processing/controlling unit 10 can be created using a general-purpose personal computer (PC) as the main component. In this case, the aforementioned functions can be realized by executing a dedicated controlling/processing software program on the PC. Additionally, an operation unit 15 with a keyboard, pointing device (e.g. a mouse) or the like is connected to the processing/controlling unit 10. With this operation unit 15, users can set various conditions for preparative separation.

Figure 2:
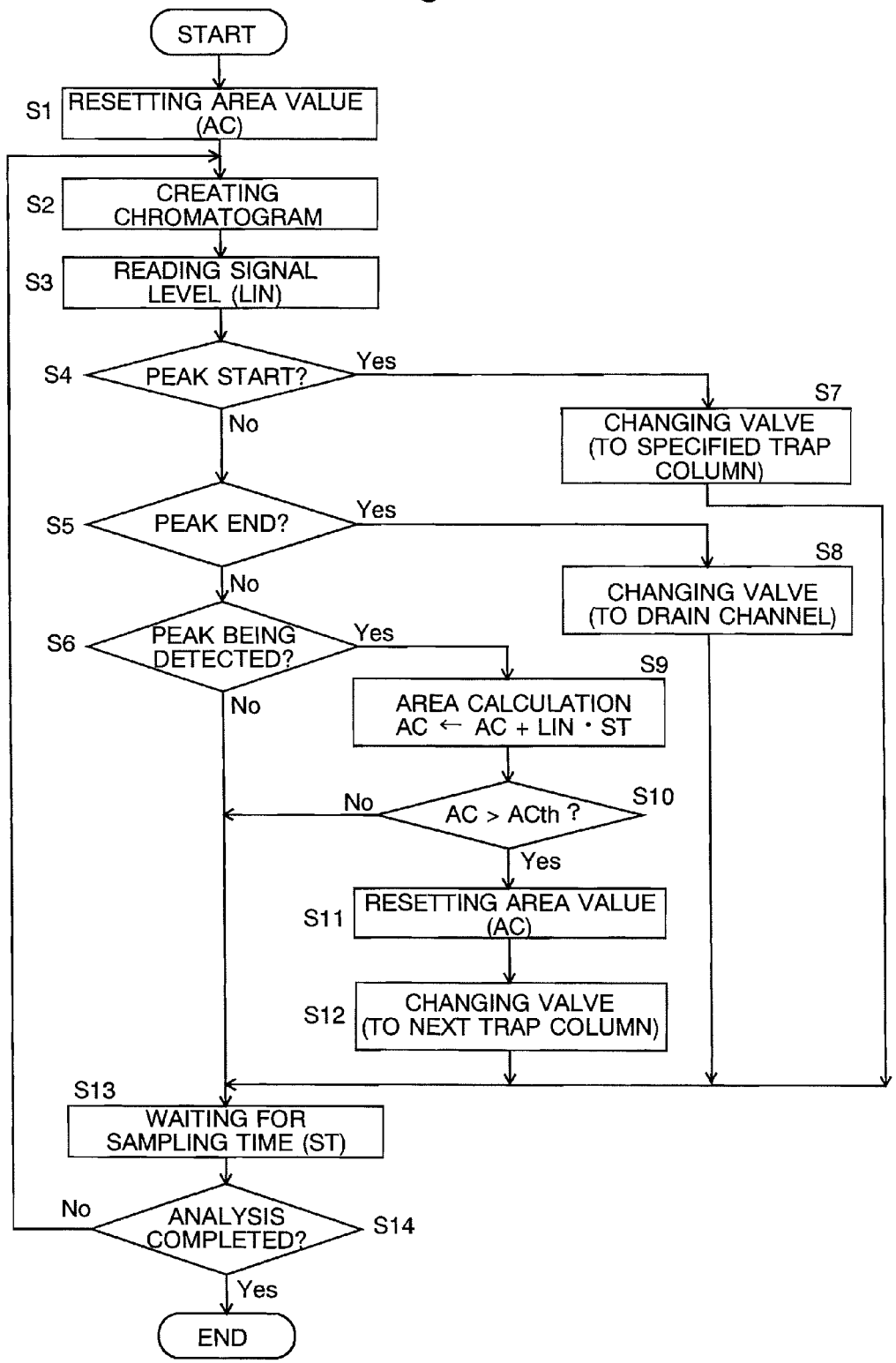
FIG. 2 is a flowchart showing the controlling and operating process for the preparative separation by the preparative LC system of the present embodiment.
Figure 3:
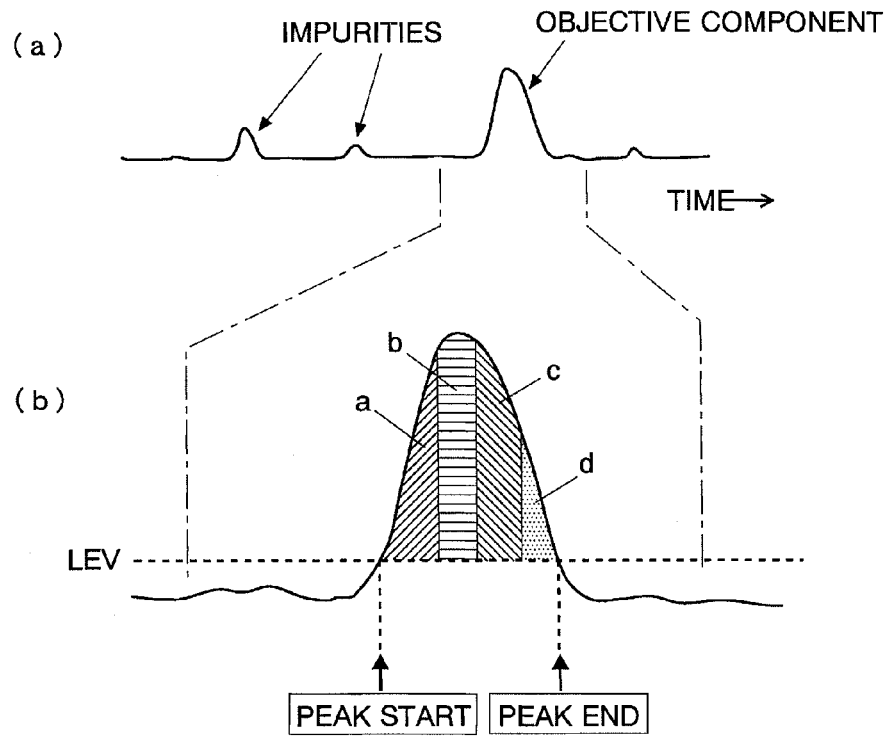
FIG. 3 is a waveform diagram illustrating the preparative separation of a component in the preparative LC system of the present embodiment.

A characteristic operation of the preparative LC system according to the present embodiment is hereinafter described with reference to the flowchart of FIG. 2 and waveform diagram of FIG. 3. The following description assumes the case of separating one known kind of objective component contained in a sample.

Before the analysis is initiated, a user (i.e. a person in charge of the analysis) sets the preparative separation conditions through the operation unit 15. For example, these conditions include the quantity of the objective component to be collected in each trap column, an approximate retention time of the objective component, and the peak detection conditions. There are generally two peak detection methods: In one method, a portion of the chromatogram where the signal level is greater than a specified threshold LEV is regarded as a peak. In the other method, the start of a peak is determined by detecting the point where the slope of the positive tangent line of a curve of the chromatogram exceeds a predetermined value, and the end of the same peak is determined by detecting the point where the slope of the negative tangent line of the same curve reaches a predetermined small value after passing a predetermined transient larger value. The two peak detection methods can be independently used or combined together. The following description assumes that the peak is detected by simply checking the signal level with reference to the threshold LEV. Naturally, the peak detection method is not limited to this one. If the retention time of the objective component is unknown, it is preferable to previously determine an approximate retention time by a preparatory analysis or the like.

In the processing/controlling unit 10, the peak detector 12 memorizes the peak detection conditions, retention time and other pieces of information that have been set. The peak area processor 13 sets a threshold ACth of the area value (to be described later) corresponding to the specified component quantity, and memorizes the threshold. When, as explained earlier, a sample is injected into the mobile phase supplied from the liquid supply pump 2 and the analysis is initiated, the peak area processor 13 resets the area value AC to be used in the subsequent calculations (Step S1). Before the analysis is initiated, the valve switching controller 14 sets the channel selection valve 6 so that an eluate that has passed through the detector 5 will flow into the drain channel 8.

Simultaneously with the initiation of the analysis, the chromatogram creator 11 begins to create a chromatogram based on the detection signals received from the detector 5 (Step S2). As a result, a chromatogram as shown in FIG. 3(a) is obtained in real-time. The peak detector 12 reads the signal level LIN of the chromatogram (Step S3) to determine whether the current point is the start point of the peak of the objective component (Step S4). As already explained, this determination of the start point of the peak is made by comparing the signal level LIN with the threshold LEV. Whether or not the detected peak is the peak of the objective component is determined with reference to the previously set approximate retention time.

If it has been determined that the current point is not the start point of the peak of the objective component, the peak detector 12 determines whether the current point is the end point of the peak of the objective component (Step S5). This determination of the end point of the peak is also made by comparing the signal level LIN with the threshold LEV. If it has been determined that the current point is neither the start point nor end point of the peak of the objective component, the peak detector 12 determines whether a peak is currently being detected, i.e. whether the current point is within the period from the start point to end point of the peak (Step S6). If the determination results in Steps S4 through S6 are all "No", it means that the current point is not within the period corresponding to the peak of the objective component. Accordingly, the peak detector 12 waits for the specified sampling time ST (Step S13), and then determines whether the analysis has been completed (Step S14). If the analysis has not been completed, the operation returns to Step S2.

As shown in FIG. 3(a), even if a peak has been found in the chromatogram, if the peak is not determined to be the peak of the objective component but the peak of an impurity, the operation proceeds from S4 through S6 to S13. Therefore, the eluate that has passed through the detector 5 flows through the channel selection valve 6 into the drain channel 8, to be discharged from the discharge port 9.

When the objective component in the sample eluted from the separation column 4 reaches the detector 5, the peak of the objective component begins to appear, as shown in FIGS. 3(a) and 3(b). Then, the peak detector 12 determines that this is the start point of the peak of the objective component, and the valve switching controller 14 changes the channel selection valve 6 so that the eluate will flow to a previously specified trap column, e.g. the first trap column 7a (Step S7). As a result, the eluate flows into the trap column 7a, and the objective component in the eluate is captured by the packing material within the trap column 7a. After the objective component is thus removed, the eluate is discharged from the discharge port 9.

After the current point has been determined to be the start point of the peak, the peak detector 12 waits for the sampling time ST and returns to Step S2. Subsequently, in Step S6, the peak detector 12 determines that a peak is currently being detected. Then, the peak area processor 13 calculates a new value of the area AC by multiplying the signal level LIN by the sampling time ST and adding the resultant value to the previous value of the area AC (Step S9). This means that the calculated value shows the peak area that has been accumulated since the last resetting of the area value AC. Subsequently, the peak area processor 13 determines whether the new value of the area AC is greater than the initially set threshold ACth (Step S10). If the new value is not greater than the threshold, the operation proceeds to Step S13. Thus, the peak area processor 13 repeats the sequence of Steps S2 through S6, S9, S10, S13 and S14 until the area value AC exceeds the threshold ACth, and then resets the area value AC when this value has exceeded the threshold ACth (Step S11). Meanwhile, the valve switching controller 14 changes the channel selection valve 6 so that the destination of the eluate switches to the next trap column, e.g. from the first trap column 7a to the second trap column 7b (Step S12).

Immediately after the destination of the eluate is changed to a new trap column, the peak detector 12 waits for the sampling time ST and returns to Step S2. Then, in Step S6, it is once again determined that a peak is currently being detected. This time, since the area value AC has been reset immediately before, the operation proceeds through Steps S9, S10 and S13, thus repeating the sequence of Steps S2 through S6, S9, S10, S13 and S14 until it is determined in Step S10 that the area value AC has exceeded the threshold ACth. When it is determined by the peak detector 12 that the end point of the peak of the objective component has been reached, the operation proceeds from Step S5 to Step S8, where the channel selection valve 6 is switched so that the eluate will flow to the drain channel 8. If there is only one kind of objective component, the analysis can be completed anytime after the objective component has been entirely eluted. If there are two or more kinds of objective components, the system may return to Step S2 to repeat the same processing and controlling operations as described previously.

In the previously described processing and controlling operations, the destination of the eluate is changed from one trap column to the next every time the area value AC of the peak exceeds the threshold ACth while one kind of objective component is being detected. That is, as shown in FIG. 3(b), in the peak of an objective component on the chromatogram, the portions of the eluate corresponding to the regions denoted by a, b and c having the same area are respectively directed to the first, second and third trap columns 7a, 7b and 7c, and the objective component contained in each portion of the eluate is captured by the packing material in each of the trap columns 7a to 7c. Since the aforementioned area corresponds to the amount of the objective component, the same quantity of the objective component will be captured by each of the trap columns 7a to 7c. However, the fourth trap column 7d, to which the eluate was still being supplied when it was determined that the end point of the peak had been reached, may possibly contain a smaller quantity of the objective component than the other trap columns 7a to 7c. Given this possibility, it is preferable to present visual information or the like to advise the user of the possibility that the quantity of the objective component captured in the fourth trap column 7d may be smaller than the required quantity.

In the preceding example, the same quantity of the objective component is captured in each of the three trap columns 7a to 7c. By performing the elution of the objective component and vaporization of the solvent on these trap columns as in Steps S21 and S22, it is possible to obtain the objective component separated into equal aliquots.

A trap column normally has the maximum capacity for capturing a component. After the maximum quantity of the component is captured in the trap column, if an eluate containing the same component is additionally supplied, the component will no longer be captured but simply flow away. To avoid this waste, the system should preferably be designed so that the quantity of the component to be captured in each trap column, which is set in the preparative separation conditions, is limited to be equal to or below the maximum capturing capacity of the trap column.

The system using the trap columns to selectively capture only the objective component is advantageous over the system that separates an eluate containing the objective component and collect it in a test tube or similar container. That is, if the sample has a low concentration of the objective component, it is necessary to use a large amount of eluate to collect the same amount of the objective component. In the case of collecting the eluate in the container, if an unexpectedly large amount of the eluate is supplied, the eluate may possibly overflow the container, impeding the collection of the specified quantity of the component. By contrast, in the case of supplying the eluate through the trap column to collect only the objective component, the solution from which the component has been removed by the trap column will be entirely discharged, so that no problem will arise even if a large amount of eluate is supplied.

The previously described embodiment is a mere example of the present invention, and any change, modification or addition that is appropriately made within the spirit of the present invention will naturally fall within the scope of the claims of this patent application.

What is claimed is:

1. A preparative liquid chromatograph system having a liquid chromatograph including a column for separating a component from a separation sample and a detector for detecting the component contained in an eluate coming from the separation column, a plurality of trap columns for trapping the component contained in the eluate, and a channel selector for switching a channel so that the eluate is selectively supplied to one of the trap columns, comprising:
   a) a chromatogram creator for creating a chromatogram during a chromatographic analysis of the sample, based on a detection signal produced by the detector;
   b) a peak area calculator for performing a real-time calculation of an area value of a peak of an objective component appearing on the chromatogram, the calculation starting from a point in time where the channel is switched by the controller to be mentioned below; and
   c) a controller for controlling the channel selector so that a destination of the eluate coming from the column is changed from one trap column to another every time the area value calculated by the peak area calculator reaches a predetermined value.

2. The preparative liquid chromatograph system according to claim 1, further comprising an input section for setting preparative separation conditions at least including a quantity of the objective component to be captured in each trap column, wherein the controller determines, based on the quantity that has been set through the input section, a reference value for making a determination on the area value calculated by the peak area calculator.

3. The preparative liquid chromatograph system according to claim 2, wherein the preparative separation conditions include an approximate retention time of the objective component.

4. The preparative liquid chromatograph system according to claim 2, wherein the preparative separation conditions include peak detection conditions.

5. The preparative liquid chromatograph system according to claim 4, wherein the peak detection conditions include a threshold level to be referenced for detecting a peak on the chromatogram.

6. The preparative liquid chromatograph system according to claim 1, further comprising a notifying section for advising a user of a possibility that the quantity of the objective component captured in one or more of the trap columns may be smaller than a required quantity.

7. A preparative separation/purification method using the preparative liquid chromatograph system according to claim 1, comprising:
   a separation process in which an objective component is captured in each of the trap columns by the preparative liquid chromatograph system;
   an elusion process in which a solvent is supplied to each of the trap columns to elute the objective component captured in the trap columns; and
   a collection process in which a solvent contained in an eluate coming from the trap columns is vaporized to collect the objective component in a solid form for each of the trap columns.

8. A preparative separation/purification method using the preparative liquid chromatograph system according to claim 2, comprising:
   a separation process in which an objective component is captured in each of the trap columns by the preparative liquid chromatograph system;
   an elusion process in which a solvent is supplied to each of the trap columns to elute the objective component captured in the trap columns; and
   a collection process in which a solvent contained in an eluate coming from the trap columns is vaporized to collect the objective component in a solid form for each of the trap columns.

* * * * *